United States Patent [19]

Dappen

[11] 4,098,574

[45] Jul. 4, 1978

[54] GLUCOSE DETECTION SYSTEM FREE FROM FLUORIDE-ION INTERFERENCE

[75] Inventor: Glen Marshall Dappen, Webster, N.Y.

[73] Assignee: Eastman Kodak Company, Rochester, N.Y.

[21] Appl. No.: 821,028

[22] Filed: Aug. 1, 1977

[51] Int. Cl.² .................... G01N 21/06; G01N 33/16
[52] U.S. Cl. ............................. 23/230 B; 23/253 TP; 195/103.5 C
[58] Field of Search ...................... 23/230 B, 253 TP; 195/103.5 C

[56] References Cited

U.S. PATENT DOCUMENTS

| | | | |
|---|---|---|---|
| 2,982,700 | 5/1961 | Adams, Jr. | 23/230 B |
| 3,104,209 | 9/1963 | Scott | 23/253 TP X |
| 3,884,764 | 5/1975 | Goodhue et al. | 195/103.5 R |
| 3,886,045 | 5/1975 | Melattini | 195/103.5 |
| 3,983,005 | 9/1976 | Goodhue et al. | 195/103.5 R |
| 3,992,158 | 11/1976 | Przybylowicz et al. | 23/253 TP |

*Primary Examiner*—Robert M. Reese
*Attorney, Agent, or Firm*—Arthur L. Girard

[57] ABSTRACT

An improved multilayer element for detecting glucose in samples of biological fluid which may contain with fluoride ion as a contaminant or preservative is described. The improved element comprises a buffered Trinder's reagent, which reagent comprises glucose oxidase, peroxidase, 4-aminoantipyrine and a phenolic or naphtholic coupler, which is buffered to a pH between about 4.5 and about 6.0. Such a buffering reduces any interference which may be due to fluoride ion present in the sample under analysis.

8 Claims, 2 Drawing Figures

GLUCOSE DETECTION SYSTEM FREE FROM FLUORIDE-ION INTERFERENCE

FIELD OF THE INVENTION

The present invention relates to improved elements for the detection of glucose, especially in biological fluids, and more particularly to improved methods for the assay of glucose in aqueous solutions which may be contaminated with fluoride ion.

BACKGROUND OF THE INVENTION

The glucose oxidase method of assaying for glucose used by Trinder is well-known in the art. Such method uses reagents, which comprise glucose oxidase, a substance having peroxidase activity, 4-aminoantipyrine and a phenolic or naphtholic coupler. The method and reagents are described in detail in the following two references: Trinder, P., *Ann. Clin. Biochem.*, 6 (1969), 24, and Trinder, P., *J, Clin, Pathol.*, 22 (1969), 246.

Sodium fluoride is used as a preservative in blood and blood serum samples which are to be held for an extended period of time, i.e. up to 10 days (Henry, *Clinical Chemistry*, 2 Ed. p. 385). Such a preservative is routinely used at a level of 250 mg/dl of blood or blood serum. The addition of 250 mg/dl of sodium fluoride to blood serium has been found to decrease the apparent glucose concentration, as measured utilizing multilayer elements of the type described in U.S. Pat. No. 3,992,158, issued November 16, 1976, by 20-30 mg/dl at a concentration of 200 mg glucose/dl. This problem is compounded by the following factors: 1) the preservative is not always used and 2) when the preservative is incorporated within blood withdrawal apparatus such as found in commercial embodiments, the concentration of preservative is known only when the container is filled to capacity. Since often the containers are not filled to capacity (due to loss of vacuum) the sodium fluoride concentration may increase as much as 2-3 fold over the 250 mg/dl level.

In view of the variability in sodium fluoride concentration which may be encountered, it is clear that a need exists for a multilayer element for the analysis of glucose which exhibits reduced sensitivity to sodium fluoride.

Although the concentrations of fluoride ion used for this purpose have apparently not caused noticeable interference with prior-art methods for analyzing for glucose probably due to dilution techniques commonly used in prior art solution quantitative assays and the semi-quantitative character of prior art "dry" methods for glucose detection, it has been found that, when a Trinder's reagent system as described above is incorporated into a multilayer element of the type described in U.S. Pat. No. 3,992,158, the fluoride ion used as a preservative contributes a substantial negative bias. The presence and elimination of this bias using the method described herein will be shown in the examples below.

U.S. Pat. No. 3,992,158 issued Nov. 16, 1976, to Przybylowicz and Millikan, describes integral multilayer elements for the detection of various biological materials.

Example 3 of U.S. Pat. No. 3,992,158 describes an element for the detection of glucose using glucose oxidase, peroxidase and an indicator system of the type described herein in an element similar to that described in the instant application. However, no pH is specified for the reagent layer containing the foregoing reagent system. A layer prepared according to this example would have a pH of above about 7.0.

U.S. Pat. No. 3,983,005 issued Sept. 28, 1976, to Goodhue et al, describes in Example 3 the use of 4-aminoantipyrine and a naphtholic coupler for the detection of hydrogen peroxide produced on contact with cholesterol oxidase in an element of the type described herein. According to this example, the indicator reaction is carried out at a pH of 7.0.

U.S. Pat. No. 3,886,045 issued May 27, 1975, describes a test composition for glucose assay comprising glucose oxidase, peroxidase, sodium or potassium ferrocyanide, an aminoantipyrine and a phenolic coupler. It is disclosed that such composition, always including the ferricyanide, are useful when buffered at a pH of between about 5.5 and 8.0. There is no disclosure that compositions which omit the ferrocyanide are useful throughout this pH range. This patent also includes an extensive discussion of phenols useful in analytical reagents of the type described herein.

SUMMARY OF THE INVENTION

It has now been discovered that the aforementioned interference of fluoride ion with glucose analyses performed in integral multilayer elements of the type described in U.S. Pat. No. 3,992,158 can be reduced or eliminated by buffering the reagent composition contained therein to a pH between about 4.5 and 6.0. Although the mechanism for this reduction or elimination of fluoride interference at this pH is not completely understood, performance of the assay reactions within this pH range provides the desired reduction or elimination, as will be shown in the examples below.

DESCRIPTION OF THE PREFERRED EMBODIMENTS:

Figure 1:
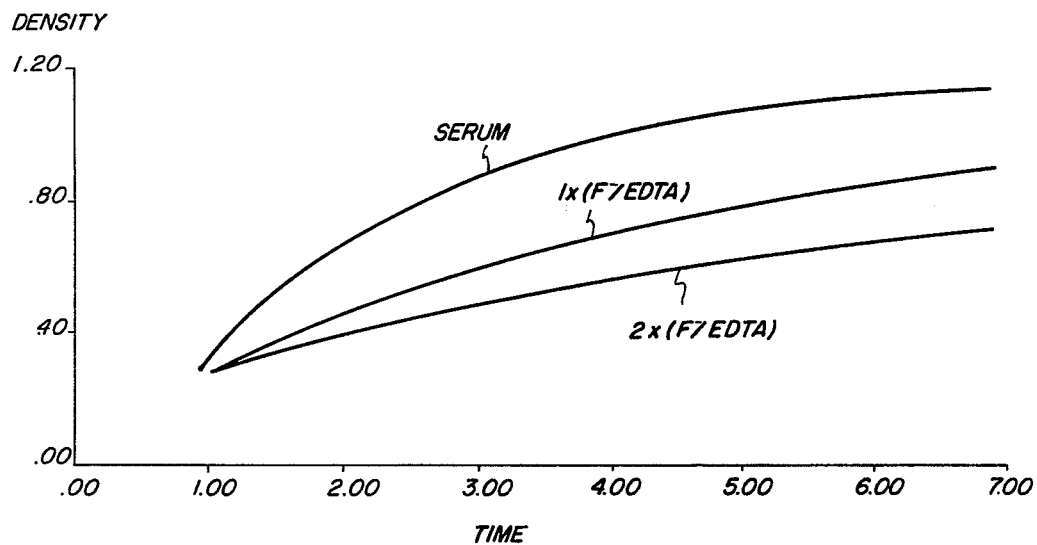

Trinder's reagent for the detection of glucose, which comprises glucose oxidase, a substance having peroxidative activity, 4-aminoantipyrine and a phenolic coupler, is well known in the art and is described in detail in the two Trinder publications referred to above.

The detection of glucose using Trinder's reagent is conventionally carried out at a pH of 7.0 or above. However, at this pH, fluoride ion, which is used as a preservative for serum samples, acts as an interferent when this reagent is used in an element of the type described in U.S. Pat. No. 3,992,158. Although the cause of this phenomenon is not understood, we have discovered that the interference due to fluoride ion in multilayer elements of the type described can be reduced or eliminated by buffering the Trinder's reagent system to a pH of between about 4.5 and 6.0.

Thus, the reagent compositions contained in the elements of the instant invention comprise Trinder's reagent or some modification thereof useful in the detection of glucose in an aqueous medium buffered to a pH of between about 4.5 and about 6.0.

Glucose oxidase and its sources and preparation are well known in the art and no further discussion thereof is required herein.

Substances having peroxidative activity which are useful in clinical applications have been discussed at length in the prior art and are well known to the skilled artisan. On such discussion is presented in U.S. Pat. No. 3,884,764 issued May 20, 1975, to Goodhue et al, at column 6, line 52, to column 7, line 18. A preferred substance of this type is, of course, peroxidase, which has been used broadly in clinical analytical applications.

Aminoantipyrine, also identified as aminophenazone, is an oxygen acceptor which, in its oxidized state, couples with a phenolic coupler. In the dry elements described herein, aminoantipyrine is generally supplied in the form of an acid salt, for example, the hydrochloride salt. A discussion of aminoantipyrine is presented in U.S. Pat. No. 3,886,045. A preferred aminoantipyrine is 4-aminoantipyrine.

A detailed discussion of phenolic couplers including examples of useful phenolic couplers is presented by Mees, C. E. K., and James, T. H., *The Theory of the Photographic Process*, Third Ed., Macmillan Co., N.Y. (1966), p. 387ff and in aforementioned U.S. Pat. No. 3,886,045. As is apparent from the discussions, phenolic couplers include both phenols and naphthols, both of which may be substituted or unsubstituted. Specifically, preferred from among such couplers is 7-hydroxy-1-naphthol. This coupler demonstrates outstanding stability and reactivity and provides an indicator dye which absorbs at a convenient wavelength for spectrophotometric measurement in the format indicated.

In order to provide an appropriate pH for the reaction to be carried out, a suitable buffer must be included in the reagent mixture. Virtually any buffer that buffers at a pH of between about 4.5 and 6.0 and is compatible with the reagent composition and suitable for incorporation in the elements described herein according to the methods described in aforementioned U.S. Pat. No. 3,992,158 is useful in the successful practice of the instant invention. Such buffers are described generally by Good, *Biochemistry*, 5, 467 (1966). Buffers that have been found useful include dimethylglutaric acids, succinic acid, malic acid, potassium acid phthalate and mixed phosphate-citrate buffers. Specifically preferred from among this group is 3,3-dimethylglutaric acid.

As used herein, the term "integral element" refers to elements having at least two superposed layers, desirably discrete, in intimate contact. Preferably, such elements are formed prior to application of a liquid sample for analysis. Elements of this invention are capable of performing internally a variety of sample-handling functions. They do not require expertise in their use and they can produce quantitative analytical results without the specialized spotting or other procedures such as sample confinement, washing or removal of excess sample, typically needed for analyses made using known elements. Further, the results produced by elements of this invention are substantially consistent and free from internal variations so that automated means of measuring electromagnetic radiation (radiometric techniques) can be used to detect such results with minimal inconsistency.

Stated more particularly, according to a preferred embodiment, the present invention provides integral analytical elements for the detection of glucose, which elements are composed of multiple, superposed layers which can provide quickly within the element a highly quantitative dye production in response to the presence of fluoride-containing solutions of glucose applied to the element. Elements of this invention include a sample spreading layer in fluid contact with a reagent layer. The sample spreading layer, synonymously referred to herein as a spreading layer or a metering layer, is capable of distributing or metering within the layer glucose contained in a liquid sample applied to the element to provide, at any given time, a uniform concentration of glucose at the surface of the spreading layer facing, i.e., closer to, the reagent layer. In various preferred embodiments, the spreading layer is isotropically porous; that is, it is porous in every direction within the layer. Reference herein to isotropic porosity identifies the fact of substantial porosity in all directions within the spreading layer. It will be understood that the degree of such porosity may be variable, if necessary or desirable, for example, regarding pore size, percentage of void volume or otherwise. It shall be understood that the term "isotropic porosity" (or "isotropically porous") as used herein should not be confused with the terms "isoporous" or "ionotropic," often used with reference to filter membranes to signify those membranes having pores that are continuous between membrane surfaces. Likewise, "isotropic porosity" should not be confused with the term "isotropic," used in contradistinction to the term "anisotropic," which signifies filter membranes having a thin "skin" along at least one surface of the membrane. See, for example, *Membrane Science and Technology*, James Flinn ed, Plenum Press, New York (1970).

The reagent layer is a layer underlying the spreading layer and containing the reagent compositions described herein, namely glucose oxidase, a substance having peroxidative activity, aminoantipyrine, a phenolic coupler and a buffer to maintain the pH of the layer between about 4.5 and 6.0 when contacted with a test sample. The reagent layer is preferably of substantially uniform permeability to glucose contained in aqueous liquid applied to the spreading layer. Uniform permeability of the layer refers to permeability such that, when a homogeneous glucose solution is provided uniformly to a surface of the layer, identical measurements of the concentration of glucose in the solution within the layer, but made through different regions of a surface of the layer, will yield substantially equal results.

Reference herein to fluid contact between a spreading layer and a reagent layer in an integral analytical element identifies the ability of a fluid, whether liquid or gaseous, to pass in such element between superposed regions of the spreading layer and the reagent layer. Stated in another manner, fluid contact refers to the ability to transport components of a fluid between the layers in fluid contact. Although such layers in fluid contact can be contiguous, they may also be separated by intervening layers. However, layers in the element that physically intervene a spreading layer and reagent layer in mutual fluid contact will also be in fluid contact and will not prevent the passage of fluid between the fluid-contacting spreading and reagent layers.

Integral multilayer elements for the detection of a variety of analytes including glucose are described in detail in U.S. Pat. No. 3,992,158 referred to hereinabove, which is expressly incorporated herein by reference. Elements of the type described therein are identical to those useful in the successful practice of the preferred embodiments hereof, and the details for preparing such elements are readily determinable therefrom.

The following examples of integral elements are provided to further illustrate the practice of the invention.

EXAMPLES 1-4

Reduced Fluoride Interference at Lower pH

Evacuated blood containers, containing either sodium fluoride/oxalate or sodium fluoride/EDTA as preservative, were partially or totally filled with blood samples; hence, the actual amount of fluoride ion present varied with each sample. If the container was totally filled (i.e., 7 cc), the amount of F⁻ present would be 250 mg/dl, if half filled, 500 mg/dl. The glucose level of each sample was brought to ~350 mg/dl by spiking. The samples were then spotted (in 10 μl aliquots) onto test elements having the following composition and which were prepared according to the methods described in U.S. Pat. No. 3,992,158.

Polyethylene terephthalate supports were coated with reagent layers comprising deionized gelatin (21.5 g/m²), peroxidase (10,000 U/m²) glucose oxidase (24,400 U/m²), 4-aminoantipyrine-HCl (0.86 g/m²), 7-hydroxy-1-naphthol (0.66 g/m²) and 3,3-dimethylglutaric acid (1.96 g/m²) (pH varied with each element as shown in Table 1). A subbing layer comprising poly-n-isopropylacrylamide and a spreading layer comprising cellulose acetate (6.6 g/m²) and $TiO_2$ (46 g/m²) were then applied.

After 7 min. at 37° C., the reflection densities produced were measured and a calibration curve of reflection density vs. glucose concentration plotted for each element. The reflection densities obtained were then checked against the derived calibration curves and the corresponding apparent glucose concentration was obtained. The difference between the glucose concentration of the calibration curves and the glucose concentration as determined according to a conventional reference method is shown in Table 1.

Table 1

| | | Fluoride Interference Studies at Various Levels of pH | | | | | |
|---|---|---|---|---|---|---|---|
| | | Fluoride/Oxalate | | | Fluoride/EDTA | | |
| Example No. | pH | Web Estimate mg./dl. | Reference mg./dl. | Bias % | Web Estimate mg./dl. | Reference mg./dl. | Bias % |
| 1 | 5.0 | 348.3 | 352.0 | −1.1 | 357.7 | 344.0 | 4.0 |
| 2 | 5.6 | 345.9 | 352.0 | −1.7 | 352.5 | 344.0 | 2.5 |
| 3 | 5.9 | 298.2 | 352.0 | −15.3 | 310.5 | 344.0 | −9.7 |
| 4 | 6.3 | 251.6 | 352.0 | −28.5 | 250.6 | 344.0 | −27.2 |

EXAMPLE 5

Effect of pH and Fluoride Interference on Rate of Development

Elements prepared in the same manner as in Examples 1–4, also varying in pH (5.0 and 7.0), were evaluated in the manner described in Examples 1–4, using serum containing no fluoride ion, plasma containing 2.5 mg/dl fluoride/EDTA and plasma containing ~5.0 mg/dl fluoride/EDTA.

Figure 2:
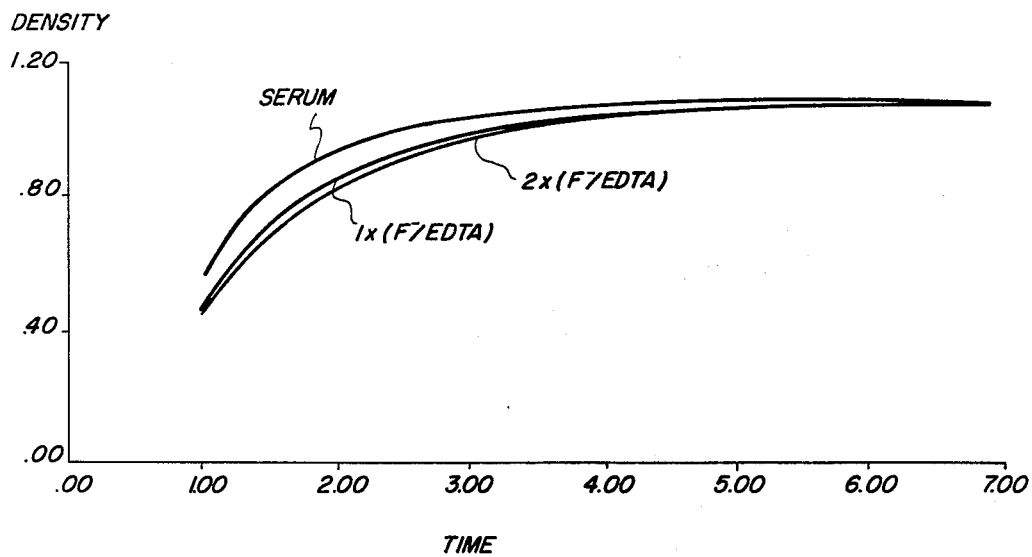

The rates of dye development ($D_R$) vs. time of the elements were compared in FIGS. 1 and 2. The rates for each sample were much slower at pH 7.0, while at pH 5.0 they differed only in the early stages of dye development.

EXAMPLES 6–11

Effect of Serum pH Upon Element Response

A series of elements was prepared as in Examples 1–4, but using three different buffer systems: dimethylglutarate (1.96 g/m²), succinic acid (1.40 g/m²) or malic acid (1.58 g/m²) (pH is indicated in Table 2).

Two samples of sera containing 100 mg/dl and 400 mg/dl glucose were each adjusted to a pH of 7.7 and 8.6. The samples were then spotted onto the test elements and evaluated as in Example 1. Results shown in Table 2 suggest that the elements, as prepared, have adequate buffering capacity and can tolerate fluctuations that may occur in the pH of serum.

Table 2

| | | | Effect of Serum pH upon Web Response | | | | | |
|---|---|---|---|---|---|---|---|---|
| | | | Serum ~100 mg./dl. | | | Serum ~400 mg./dl. | | |
| Example | pH | Buffer | pH = 7.7 | pH = 8.6 | % $\Delta D_R$ | pH = 7.7 | pH = 8.6 | % $\Delta D_R$ |
| 6 | 5.0 | DMG | .382 | .382 | 0.0 | 1.266 | 1.249 | −1.3 |
| 7 | 5.5 | DMG | .389 | .390 | +0.3 | 1.253 | 1.240 | −1.0 |
| 8 | 5.0 | succinic acid | .385 | .390 | +1.3 | 1.284 | 1.278 | −0.5 |
| 9 | 5.5 | succinic acid | .401 | .403 | +0.5 | 1.295 | 1.276 | −1.5 |
| 10 | 5.0 | malic acid | .379 | .382 | +0.8 | 1.238 | 1.228 | −0.8 |
| 11 | 5.5 | malic acid | .351 | .355 | +1.1 | 1.217 | 1.204 | −1.1 |

Although the invention has been described in considerable detail with particular reference to certain preferred embodiments thereof, variations and modifications can be effected within the spirit and scope of the invention.

We claim:

1. In a method for assaying for glucose in aqueous liquids by applying a sample of the aqueous liquid to a test element comprising a spreading layer and a reagent layer containing a reagent composition comprising a buffer, glucose oxidase, a substance having peroxidative activity and an indicator composition comprising 4-aminoantipyrine and a phenolic or naphtholic coupler such that glucose contained in the liquid sample is oxidized in the presence of said reagent composition to produce a colored product, the improvement comprising performing the said assay at a pH of between about 4.5 and 6.0 to reduce or eliminate interference with the assay due to fluoride ion which may be contained in the aqueous liquid sample.

2. The method of claim 1 wherein said substance having peroxidative activity is peroxidase.

3. The method of claim 1 wherein said coupler is 7-hydroxy-1-naphthol.

4. The method of claim 1 wherein the buffer is selected from the group consisting of dimethylglutaric acid, succinic acid, potassium acid phthalate, malic acid, and mixed phosphate-citrate buffer.

5. In an integral element for the determination of glucose in aqueous liquids comprising a spreading layer and a reagent layer in fluid contact under conditions of use and containing as the glucose determining reagent composition Trinder's reagent the improvement comprising the inclusion of a buffer which maintains the pH of the reagent composition between about 4.5 and 6.0 under conditions of use.

6. The element of claim 5 wherein said substance having peroxidative activity is peroxidase.

7. The element of claim 5 wherein said coupler is 7-hydroxy-1-naphthol.

8. The element of claim 5 wherein the buffer is selected from the group consisting of dimethylglutaric acid, succinic acid, potassium acid phthalate, malic acid, and mixed phosphate-citrate buffer.

* * * * *